United States Patent [19]
Beitelia et al.

[11] Patent Number: 5,993,460
[45] Date of Patent: Nov. 30, 1999

[54] RAPID EXCHANGE DELIVERY SYSTEM FOR STENTING A BODY LUMEN

[75] Inventors: Rainier Beitelia, San Jose; Kurt R. Klemm, Santa Clara, both of Calif.

[73] Assignee: Advanced Cardiovascular Systems, Inc., Santa Clara, Calif.

[21] Appl. No.: 09/049,309

[22] Filed: Mar. 27, 1998

[51] Int. Cl.[6] .................................................. A61M 25/10
[52] U.S. Cl. ............................................ 606/108; 606/194
[58] Field of Search .................................. 606/108, 194; 604/96

[56] References Cited

U.S. PATENT DOCUMENTS

| | | |
|---|---|---|
| 5,180,368 | 1/1993 | Garrison . |
| 5,350,395 | 9/1994 | Yock . |
| 5,360,401 | 11/1994 | Turnland . |
| 5,421,955 | 6/1995 | Lau et al. . |
| 5,451,233 | 9/1995 | Yock . |
| 5,458,615 | 10/1995 | Klemm et al. ........................... 606/198 |
| 5,496,346 | 3/1996 | Horzewski et al. . |
| 5,501,227 | 3/1996 | Yock . |
| 5,514,154 | 5/1996 | Lau et al. ................................. 606/195 |
| 5,533,968 | 7/1996 | Muni et al. . |
| 5,626,600 | 5/1997 | Horzewski et al. . |
| 5,690,644 | 11/1997 | Yurek et al. ............................. 606/108 |
| 5,780,807 | 7/1998 | Saunders . |
| 5,782,855 | 7/1998 | Lau et al. . |
| 5,827,322 | 10/1998 | Williams . |
| B1 5,421,955 | 1/1998 | Lau et al. . |

Primary Examiner—Michael H. Thaler
Attorney, Agent, or Firm—Fulwider Patton Lee & Utecht, LLP

[57] ABSTRACT

A rapid exchange catheter system provides a delivery vehicle to carry a stent through a patient's vasculature and deploy the stent after a protective sheath covering the stent has been withdrawn. In order to facilitate the rapid exchange of catheters and specifically the backloading of a catheter onto the proximal end of a guide wire, the catheter includes telescoping sleeves within the guide wire lumen that translate relative to each other as the sheath is retracted to expose the stent. The telescoping sleeves align the catheter and the sheath when the catheter is backloaded onto the distal extremity of the guide wire by aligning the guide wire notch of the catheter with an opening in the sheath thus providing a continuous guide wire passageway.

23 Claims, 2 Drawing Sheets

RAPID EXCHANGE DELIVERY SYSTEM FOR STENTING A BODY LUMEN

BACKGROUND OF THE INVENTION

The invention generally relates to vascular catheters suitable for maintaining the patency of a blood vessel after a vascular procedure therein, such as angioplasty. In particular, the present invention relates to angioplasty apparatus facilitating rapid exchanges and a method for making rapid exchanges of angioplasty devices.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having an inflatable balloon on the distal end thereof are introduced through the guiding catheter with the guide wire slidably disposed within an inner lumen of the dilatation catheter. The guide wire is first advanced out of the distal end of the guiding catheter and is then maneuvered into the patient's coronary vasculature containing the lesion to be dilated, and is then advanced beyond the lesion. Thereafter, the dilatation catheter is advanced over the guide wire until the dilatation balloon is located across the lesion. Once in position across the lesion, the balloon of the dilitation catheter is filled with radiopaque liquid at relatively high pressures (e.g., greater than about four atmospheres) and is inflated to a predetermined size (preferably the same as the inner diameter of the artery at that location) to radially compress the atherosclerotic plaque ofthe lesion against the inside of the artery wall to thereby dilate the lumen of the artery. The balloon is then deflated so that the dilatation catheter can be removed and blood flow resumed through the dilated artery.

A common problem that sometimes occurs after an angioplasty procedure is the development of restenosis at or near the site of the original stenosis in the body lumen which requires a second angioplasty procedure, a bypass surgery, or similar procedure to reduce or remove the restenosis. In recent years, various devices and methods (other than bypass surgery) for the prevention of restenosis after arterial intervention in a patient's body lumen have become known which typically use an expandable graft (commonly termed "stent") on the distal end of the catheter designed for implantation in the body lumen.

Stents generally are designed for permanent implantation within the body lumen. By way of example, several stent devices and methods can be found in commonly assigned and commonly owned U.S. Pat. No. 5,158,548 (Lau et al.); U.S. Pat. No. 5,242,399 (Lau et al.); U.S. Pat. No. 5,344,426 (Lau et al.); U.S. Pat. No. 5,514,154 (Lauetal.); U.S. Pat. No. 5,360,401 (Turnlandetal.); and U.S. Ser. No. 08/454,599 (Lam), which are incorporated in their entirety herein.

In recent years in practicing angioplasty, it is often desirable to exchange one dilatation catheter for another. In doing so, it is necessary to use extension wires or long exchange wires having a total length of approximately 200 to 300 centimeters, both of which typically require two operators. During the procedure, it is necessary that the operators communicate with each other to coordinate their efforts, which makes the procedure more involved and time consuming.

In addition, because the extension wires or exchange wires are long, they are awkward to handle. For that reason, they may come in contact with the floor or otherwise extend out of the sterile surgical field and become contaminated. If contaminated, the entire apparatus being utilized for the angioplasty procedure must be removed from the patient and replaced.

There have been improvements in the field of rapid exchange catheters to rectify some of the shortcomings. For example, U.S. Pat. No. 4,748,982 to Horzewski et al. discloses a method and apparatus relating to a rapid exchange balloon dilatation catheter with slitted exchange sleeve. The sleeve has a slit extending longitudinally from the proximal extremity of the sleeve to a region adjacent the balloon to permit the guide wire, which is used to assist guiding the catheter in to a vessel of a patient, to be removed therethrough. U.S. Pat. No. 5,040,548 to Yock discloses methods for performing angioplasty procedures within a patient's coronary artery to facilitate rapid exchanges of angioplasty devices. U.S. Pat. No. 5,180,368 to Garrison discloses a rapidly exchangeable and expandable cage catheter for repairing damaged blood vessels. Garrison discloses an intravascular catheter having an expandable cage mounted on the distal end of a tubular member that is radially expanded and contracted by means of a control wire. The device includes a flexible tubular element extending through the expandable cage interior to facilitate the rapid exchange of the catheter. U.S. Pat. No. 5,061,273 to Yock discloses another angioplasty apparatus facilitating rapid exchanges.

During rapid exchange catheter procedures known in the art, it is necessary for the surgeon to introduce the balloon dilatation catheter onto the guide wire already positioned within the body lumen by a backloading technique. Specifically, the guide wire remains stationary in the patient's vasculature while the distal extremity of the catheter is advanced over the guide wire proximal end. The guide wire proximal end exits through an opening on the outer surface of the catheter proximal to the balloon. However, threading the guide wire through this opening on the outer surface of the catheter is difficult and requires time and precision, especially when the catheter is covered by a protective sheath.

In addition, recent developments in stent delivery systems require use of a protective sheath to cover the stent during the delivery process, which sheath is retracted so the stent can be deployed. Use of such a sheath complicates the backloading of the guide wire during the rapid exchange catheter procedure because the guide wire must not only pass through the outer surface opening in the catheter, but it must also pass through a similar opening in the sheath. If the two openings are misaligned, backloading the guide wire becomes even more difficult.

Accordingly, there is a need for a rapid exchange catheter having a design that facilitates easy front loading and backloading of the catheter so that the guide wire passes through the catheter and sheath quickly and precisely without numerous attempts by the surgeon to align catheter and sheath openings to thread the guide wire therethrough.

SUMMARY OF THE INVENTION

The present invention is directed to a stent delivery system and method for delivery of an expandable stent within a body lumen. Preferably, a rapid exchange type catheter coupled with a sheath is used to deliver and implant the stent in a body lumen, such as a coronary artery. The stent delivery system preferably comprises an elongated sheath having proximal and distal portions and having a guide wire exit notch, and a catheter covered by the sheath and having proximal and distal portions with a guide wire lumen and an inflation lumen extending therethrough. The catheter includes a guide wire port in communication with the guide wire lumen, and an inflatable balloon disposed at the distal portion of the catheter. The balloon includes an interior in communication with the inflation lumen. The expandable stent is disposed on the balloon beneath the protective sheath.

A first telescoping sleeve is attached to the guide wire port where the interior of the first sleeve is in communication with the guide wire lumen. A second telescoping sleeve is slidably connected to the first telescoping sleeve, and the second sleeve is attached to the sheath such that an interior of the first sleeve is in communication with the guide wire lumen. The invention further includes a guide wire that passes through the guide wire lumen, the first and second telescoping sleeves, and exits from the sheath.

In a preferred embodiment, a manipulator handle is connected to the proximal portions of the catheter and sheath to impart relative axial movement thereto to expose the balloon and stent during delivery of the stent. The handle is flirter used to control inflation and deflation of the balloon and accordingly the proper expansion of the stent to implant it in the body lumen.

After deployment of the stent through conventional methods, the catheter is separated from the guide wire in a manner known in the art. Specifically, this special process for a rapid exchange catheter is discussed in, for example, U.S. Pat. No. 4,748,982 to Horzewski et al., which is incorporated herein by reference.

When it is desired to exchange a rapid exchange dilatation catheter (not shown) for the rapid exchange stent delivery catheter of the invention, the guide wire is retained in its position in the patient and the dilatation catheter is removed by withdrawing same until the guide wire exit notch appears outside of the guiding catheter. Thereafter, as the catheter is withdrawn, the guide wire can be pulled out through a slit formed in the side of the catheter until the catheter has been withdrawn to a point just proximal of the balloon. Thereafter, the catheter can be withdrawn on the guide wire until the balloon clears a rotating hemostasis valve which is attached to the proximal end of the guiding catheter. The dilatation catheter is then removed from the guide wire and the stent delivery catheter is threaded onto the proximal end of the guide wire and advanced through the rotating hemostasis valve and over the guide wire which is still in position inside the patient.

In order to insert the stent delivery catheter into the patient in this rapid exchange procedure, the guide wire is introduced into the stent delivery catheter by a back-loading technique, wherein the proximal end of the guide wire is inserted through the distal end of the catheter, and into the guide wire lumen. The guide wire is held stationary while the distal portion of the catheter is advanced over the guide wire until the guide wire is guided through the first and second telescoping sleeves, attached to the guide wire lumen, and out the guide wire exit notch in the sheath. The telescoping sleeves of the present invention thus guide the proximal end of guide wire out of the catheter and sheath with precision and without multiple attempts by the physician to try to align the exit ports on the catheter and the sheath.

An important aspect of the invention is that the telescoping feature of the sleeves permits the use of a sliding sheath that is initially used to protect the stent during delivery. The sleeves ensure that the proximally located guide wire port and the sheath opening are aligned so that the proximal extremity of the guide wire can be threaded therethrough, despite displacement of the sheath proximally relative to the catheter. Because one segment of the complementary telescoping sleeves is affixed to the sheath and the other complementary segment is affixed to the catheter, the movement of the sheath proximally relative to the catheter creates the telescoping action of the sleeves. So despite movement of the sheath relative to the catheter, the telescoping sleeves ensure that there is an uninterrupted passageway that is in communication with the guide wire lumen to permit passage of the guide wire through the sheath opening. In view of the foregoing, it is therefore an important aspect of the present invention to provide an assembly for easy backloading of a rapid exchange catheter onto a guide wire in position in the patent. It is also desired to provide a mechanism in a rapid exchange catheter employing a protective sheath that moves axially relative to the catheter during deployment of an expandable stent. It is yet another advantage of the present invention to employ telescoping sleeves that are in communication with a guide wire lumen inside the catheter to provide alignment between the sheath and catheter to permit passage of the proximal extremity of the guide wire therethrough during a backloading procedure. These and other advantages of the present invention will become apparent from the following detailed description thereof when taken in conjunction with the accompanying exemplary drawings.

DETAILED DESCRIPTION OF THE PREFERRED EMBODIMENTS

The present invention is directed to a stent delivery system for delivery of an expandable stent within a body lumen. In particular, the present invention is directed to a rapid exchange balloon catheter wherein the balloon carries a stent which is covered by a retractable sheath, and wherein the catheter includes telescoping sleeves in communication with a guide wire lumen so that during a rapid exchange procedure of the catheter, the catheter can be backloaded onto the guide wire quickly since the sheath and catheter are aligned to permit the guide wire to exit easily.

While the invention is described in detail as applied to coronary arteries, those skilled in the art will appreciate that it can be used in other body lumens as well, such as in peripheral arteries and veins. Where different embodiments have like elements, like reference numbers have been used.

Figure 1:
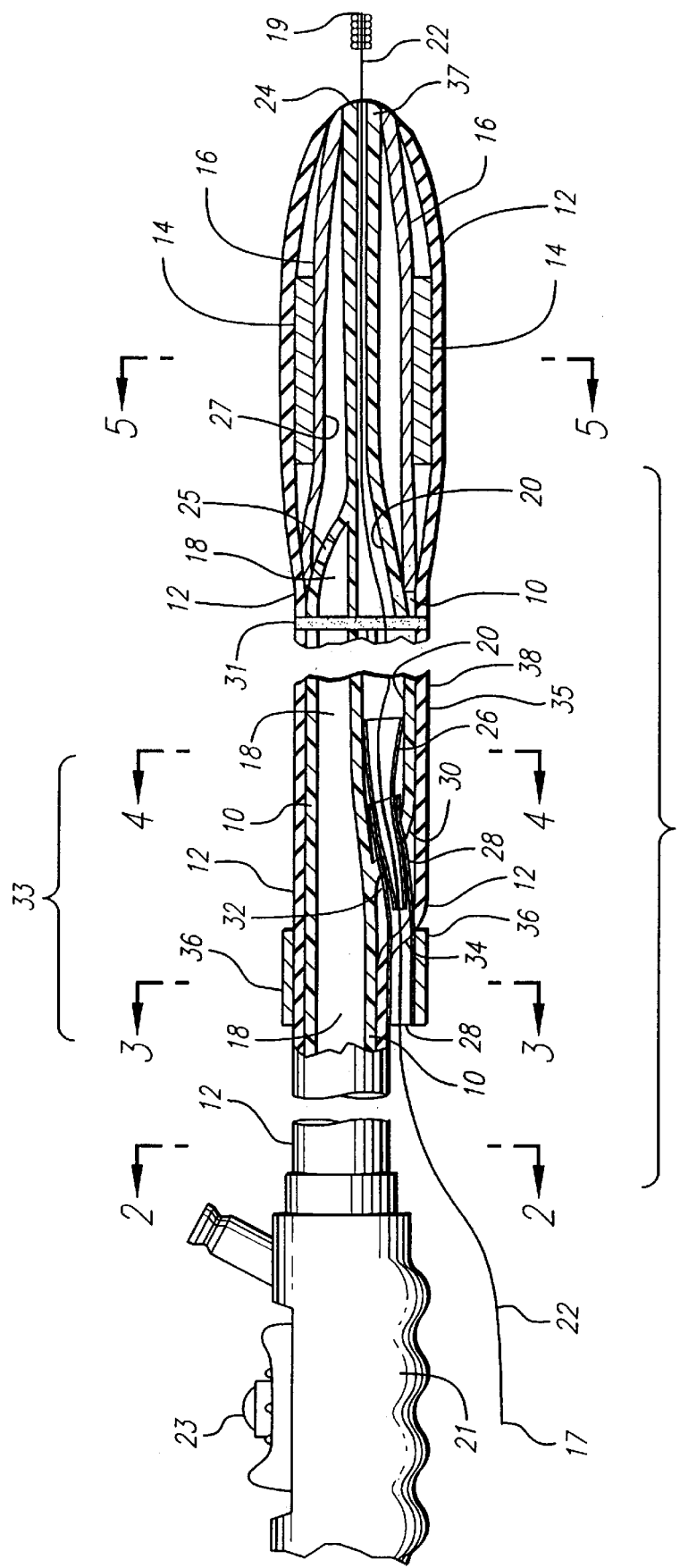
FIG. 1 is a side elevational view, partially in cross-section, depicting an intravascular catheter having rapid exchange design employing features of the present invention.
Figure 5:
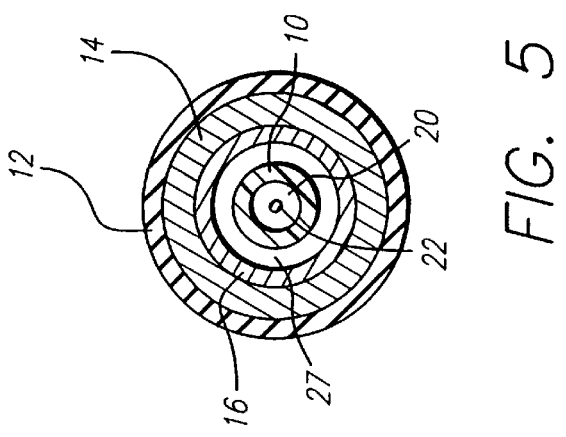
FIG. 5 is a cross-sectional view taken along the line 5—5 of FIG. 1.

FIG. 1 is a side elevational view, partially in cross-section, of a preferred embodiment of the present invention. In particular, FIG. 1 illustrates an elongated catheter 10 suitable for rapid exchange procedures known in the art. Such rapid exchange catheters are taught in, for example, U.S. Pat. No. 4,748,982 to Horzewski et al., mentioned above. The catheter 10 has an elongated shape, generally about 135 cm, and is substantially covered by retractable sheath 12. The retractable sheath 12 covers stent 14 and balloon 16 and provides a means for protecting and safely delivering stent 14 through the vasculature. As is known, once the stent 14 is positioned at the desired location in the body lumen, the sheath 12 is retracted to uncover stent 14, and balloon 16 is then inflated to expand the stent 14 and implant it in the body lumen.

As seen in FIGS. 1–4(a), catheter 10 is a side-by-side lumen design wherein the inflation lumen 18 is adjacent and parallel to guide wire lumen 20.

The present invention preferably includes guide wire 22 that passes through distal guide wire port 24 at a distal portion of catheter 10. The guide wire lumen 20 of the present invention generally extends through about the distal most 10 to 50 cm of the 135 cm catheter 10. At about point 33 of the catheter 10, the present invention includes telescoping sleeves 26, 28 through which the guide wire 22 passes. Telescoping sleeve 26 preferably protrudes into the catheter 10 a short distance via guide wire exit port 30 at guide wire notch 32 formed in the catheter 10. This can be seen in FIGS. 2–5, which provide cross-sectional views of the catheter 10 at various locations.

Figure 3:
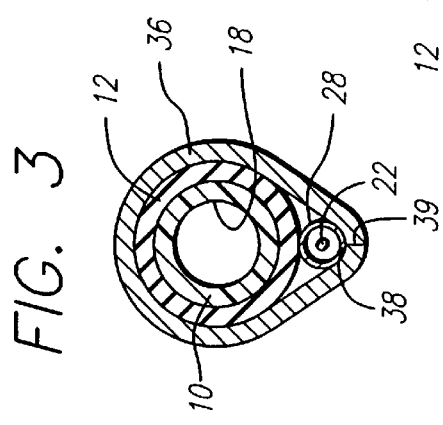
FIG. 3 is a cross-sectional view taken along the line 3—3 of FIG. 1.
Figure 2:
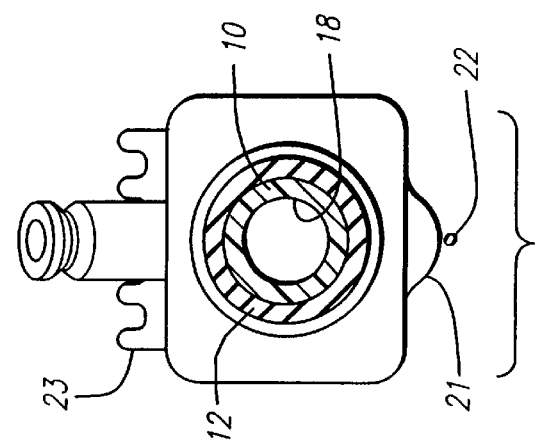
FIG. 2 is a cross-sectional view taken along the line 2—2 of FIG. 1.

The sheath 12 also includes guide wire exit port 34 through which the sleeve 28 passes. Once it emerges outside of the catheter 10 and sheath 12, sleeve 28 is held against the outer wall of the sheath 12 by adhesively bonding it to the sheath 12 outer wall or by wrapping it with an optional external sleeve 36. FIG. 3 depicts a cross-sectional view of the external sleeve 36 and telescoping sleeve 28. As seen in FIG. 1, the guide wire 22 includes a proximal extremity 17 and a distal extremity 19 that are free and clear of the catheter 10.

A manipulator handle 21 is connected to the catheter 10 and sheath 12. The manipulator handle 21 is similar to that disclosed in, for example, U.S. Pat. Nos. 5,391,172 to Williams et al. and 5,458,615 to Klemm at al., the entire contents of which are incorporated by reference herein. Other manipulator handles known in the art may be used as well. As seen in FIG. 1, a reciprocating push-button slide switch 23 on the handle 21 is used to retract the sheath 12 proximally to expose the stent 14 at the deployment site as explained above. To prevent unexpected movement of the sheath 12, the push-button slide switch 23 can be mechanically locked in place so that it does not shift.

An inflation fluid is injected through a Luer lock (not shown) at the proximal end of the handle 21. The fluid flows through the Luer lock, the inflation lumen 18 of the catheter 10, and into the interior 27 of the balloon 16, thus expanding the balloon 16.

Figure 4A:
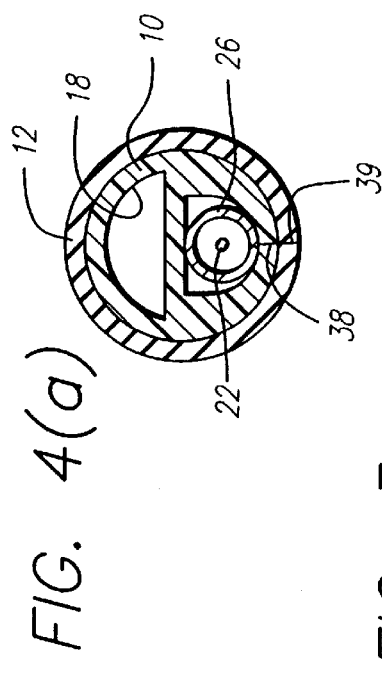
FIG. 4(a) is a cross-sectional view taken along line 4—4 of FIG. 1.
Figure 4B:
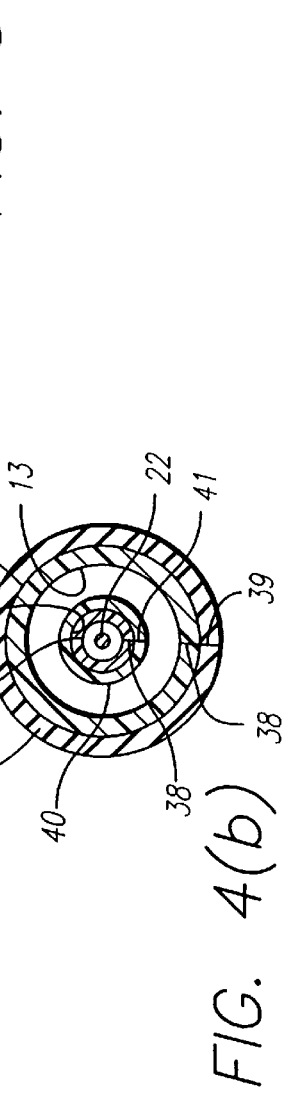
FIG. 4(b) is a cross-sectional view of an alternative embodiment showing a coaxial-type catheter having a guide wire lumen that is coaxial with the inflation lumen.

As seen in FIG. 4(b), in an alternative embodiment, catheter 11 has an inflation lumen 13 that is coaxial with guide wire lumen 15. In the FIG. 4(b) view, guide wire 22 extends through guide wire lumen 15 and sleeve 26. Guide wire lumen 15 is formed by inner member 40 which also has a rapid exchange slit 41 that the guide wire pulls through.

The preferred method of use of the present invention is described as follows. A guiding catheter, known in the art, is first introduced into the vasculature through conventional methods. An elongated catheter of the appropriate size is selected and, along with a guide wire, are introduced into the guiding catheter by preferably first advancing the guide wire past the stenosis and thereafter advancing the catheter so that a dilatation balloon is positioned within the stenosis. Thereafter, the balloon is inflated in a conventional PTCA manner.

In keeping with the preferred method, the dilatation catheter is withdrawn from the patient and stent delivery catheter 10 is inserted. Distal end 37 of catheter 10 is threaded over proximal end 17 of guide wire 22 which remains stationary in the patient. Catheter 10 is advanced distally over guide wire 22. Telescoping sleeves 26, 28 help guide the proximal extremity 17 of guide wire 22 through the guide wire lumen 20, guide wire notch 32, sheath opening 34, and finally emerging out of sheath 12. The preferred method allows the stent delivery catheter to be backloaded more easily because the telescoping sleeves prevent the proximal extremity 17 of guide wire 22 from hanging up at the sheath opening 34 by providing perfect alignment with the guide wire notch 32.

Catheter 10 is then advanced over the guide wire and once the stent 14 and underlying balloon 16 are in position within the body lumen, the sheath 12 is retracted, exposing the stent 14. Inflation fluid is inserted through inflation lumen 18, which inflation fluid flows through opening 25 and into the interior 27 of the inflation balloon 16. Internal pressure of the inflation balloon 16 inflates the balloon thereby expanding the stent 14.

In keeping with the preferred method, as the sheath 14 is withdrawn proximally, it translates telescoping sleeve 28 relative to telescoping sleeve 26. This occurs because sleeve 28 is attached to the sheath 12 by use of an optional external sleeve 36 wrapped thereon, by use of a bonding agent at one or more contact points between the sleeve 28 and the sheath 12, or both. Sleeve 26 translates relative to sleeve 28 since sleeve 26 is bonded to the guide wire lumen 20. As a result, retracting the sheath 12 causes a telescoping action between the sleeves 26,28 with the overall length of the telescoping sleeves 26, 28 increasing as the sheath 12 is retracted. The increasing length of the sleeves 26,28 is proportional to the amount of axial movement the sheath 12 undergoes to expose stent 14, generally about 20–40 mm proximally.

After the stent has been implanted in the body lumen, the catheter is removed from the patient. As seen in FIG. 1, the guide wire 22 emerges from the guide wire notch 32 outside of the sheath 12 through sheath opening 34. The catheter 10 can be removed from the guide wire 22 by pulling the guide wire 22 out through slit 38, which is formed in the catheter outer wall and extends longitudinally from the guide wire port 30 to a region 35 just proximal of the inflation balloon 16. Sheath 12 and external sleeve 36 also both have a slit 39, seen in FIGS. 3 and 4, which extends from sleeves 26, 28 to a point corresponding with slit 38 in catheter 10. Thus, guide wire 22 pulls through slit 39 and catheter slit 38 to effect the rapid exchange procedure. Of course, sleeves 26,28 also have slit 38 to permit the guide wire to be pulled therethrough during the catheter exchange.

By the described method it can be seen that it is possible to accomplish the rapid exchange of a catheter by merely making the exchange over a very short length, such as 10–50 centimeters of the distal portion of the catheter. Thus, with the catheter of the present invention, it is possible to utilize conventional guide wires without the necessity of long exchange wires as has been the practice in the past. In addition, it has been possible to accomplish such an exchange utilizing a stent carrying balloon catheter that incorporates a protective sheath.

In the preferred embodiment, the telescoping sleeves are made from a polyimide tubing. The external sleeve is preferably made from polyether ether ketone tubing. The bonding agent used to bond the telescoping sleeves to the sheath and catheter is preferably polymethylmethacrylate or its equivale. The balloon 16 is made from a material such as polyethylene.

The sheath 12 may preferably include one or more radiopaque markers 31 and the balloon 16 may have one or more radiopaque markers to assist in positioning those structures within the patient's vessels.

It is recognized that other modifications can be made to the present invention without departing from the scope thereof. The specific dimensions, inflation times, and materials of construction are provided as examples and substitutes are readily contemplated which do not depart from the invention.

What is claimed is:

1. A stent delivery system for delivery of an expandable stent within a body lumen, comprising:
   an elongated sheath having proximal and distal portions and having a guide wire exit port;
   a catheter, substantially covered by the sheath, and having a proximal and a distal portion with a guide wire lumen and an inflation lumen extending therethrough, the catheter including a guide wire port in communication with the guide wire lumen;
   an inflatable balloon disposed at the distal portion of the catheter, wherein the balloon includes an interior in fluid communication with the inflation lumen, and where in an expandable stent is disposed on the balloon beneath the sheath;
   a first telescoping sleeve, attached to the catheter guide wire port, wherein an interior of the first sleeve is in communication with the guide wire lumen;
   a second telescoping sleeve slidably connected to the first telescoping sleeve, the second sleeve being attached to the sheath such that an interior of the second sleeve is in communication with the guide wire lumen;
   a guide wire passing through the guide wire lumen, the first and second telescoping sleeves, and out of the sheath guide wire exit port; and
   a manipulator handle connected to the proximal portions of the catheter and sheath imparting relative axial movement thereto to expose the balloon and stent.

2. The stent delivery system of claim 1, wherein the catheter includes a slit extending longitudinally from the guide wire port to a region proximal of the balloon to facilitate removal of the guide wire therethrough.

3. The stent delivery system of claim 1, wherein the guide wire lumen extends within and is coaxial with the inflation lumen.

4. The stent delivery system of claim 1, wherein the guide wire lumen extends in parallel with the inflation lumen.

5. The stent delivery system of claim 1, wherein the first telescoping sleeve is bonded to the catheter, and the second telescoping sleeve is bonded to the sheath.

6. The stent delivery system of claim 1, wherein the system further comprises an external sleeve disposed over the second telescoping sleeve.

7. The stent delivery system of claim 1, wherein the first and second telescoping sleeves are formed from a polyimide tubing.

8. The stent delivery system of claim 1, wherein the sheath and the first and second telescoping sleeves have a slit for pulling the guide wire therethrough during a catheter exchange.

9. A stent delivery system for delivery of an expandable stent within a body lumen, comprising:
   an elongated sheath having a proximal portion, a mid-portion, and a distal portion and having a guide wire exit port at the mid-portion;
   a catheter, at least partially covered by the sheath and having a proximal portion, a mid-portion, and a distal portion with a guide wire lumen and an inflation lumen extending at least partially therethrough, the catheter including a guide wire port at the mid-portion thereof in communication with the guide wire lumen;
   an inflatable balloon disposed at the distal portion of the catheter, wherein the balloon includes an interior in fluid communication with the inflation lumen, and wherein the expandable stent is disposed on the balloon beneath the sheath;
   a first telescoping sleeve attached to the catheter guide wire port, wherein an interior of the first sleeve is in communication with the guide wire lumen;
   a second telescoping sleeve slidably connected to the first telescoping sleeve, the second sleeve being attached to the sheath such that an interior of the second sleeve is in communication with the guide wire lumen;
   a guide wire passing through the guide wire lumen, the first and second telescoping sleeves, and out of the sheath guide wire exit port;
   a slit in the catheter extends longitudinally from the guide wire port to a region adjacent the balloon to facilitate removal of the guide wire therethrough; and
   a manipulator handle connected to the proximal portions of the catheter and sheath imparting relative axial movement thereto to expose the balloon and stent.

10. The stent delivery system of claim 9, wherein the guide wire lumen extends within and is coaxial with the inflation lumen.

11. The stent delivery system of claim 9, wherein the guide wire lumen extends side-by-side with the inflation lumen.

12. The stent delivery system of claim 9, wherein the first telescoping sleeve slides coaxially into the second telescoping sleeve for relative telescoping action.

13. The stent delivery system of claim 9, wherein the system further comprises an external sleeve disposed over the second telescoping sleeve and bonded thereto.

14. The stent delivery system of claim 13, wherein the external sleeve is formed from a polyether ether ketone.

15. The stent delivery system of claim 9, wherein the first telescoping sleeve is attached to the catheter guide wire port with an adhesive.

16. The stent delivery system of claim 9, wherein the sheath and the first and second telescoping sleeves each have a slit to facilitate catheter exchanges.

17. A method for delivering an expandable stent within a body lumen, comprising the steps of:
   providing an elongated sheath having proximal and distal portions and having a guide wire exit port;
   covering a catheter with the sheath, wherein the catheter includes proximal and distal portions with a guide wire lumen and an inflation lumen extending therethrough, the catheter including a guide wire port in communication with the guide wire lumen;
   providing an inflatable balloon disposed at the distal portion of the catheter, wherein the balloon includes an interior in fluid communication with the inflation lumen, and wherein the expandable stent is disposed on the balloon beneath the sheath;
   providing a first telescoping sleeve, attached to the catheter guide wire port, wherein an interior of the sleeve is in communication with the guide wire lumen;
   providing a second telescoping sleeve slidably connected to the first telescoping sleeve, the second sleeve being attached to the sheath such that an interior of the sleeve is in communication with the guide wire lumen;

inserting a guide wire through the guide wire lumen, the first and second telescoping sleeves, and out of the sheath guide wire exit port;

providing a slit in the catheter extending longitudinally from the guide wire port to a region adjacent the balloon to facilitate removal of the guide wire therethrough; and operating a manipulator handle connected to the proximal portions of the catheter and sheath to impart relative axial movement thereto to expose the balloon and stent within the body lumen and to retract one of the first and second telescoping sleeves relative to the other of the first and second telescoping sleeves.

18. The method according to claim 17, further comprising providing a slit in the sheath and the first and second telescoping sleeves to facilitate catheter exchanges.

19. The method according to claim 18, wherein the method further comprises the steps of withdrawing the catheter from the body lumen, pulling the catheter away from the guide wire along the catheter slit and the sheath and first and second telescoping sleeve slits, and separating the catheter from the guide wire.

20. The method according to claim 17, wherein the method further comprises the step of inflating the balloon to expand the stent into contact with the body lumen.

21. An apparatus for aligning a catheter and a protective sheath, comprising:

a catheter having a distal end and a proximal end, the catheter having a guide wire lumen extending for at least a portion therein and an expandable member positioned near the distal end;

a protective sheath positioned over the catheter and configured for relative axial movement with the catheter;

a first telescoping sleeve extending from the guide wire lumen out of a guide wire port on an outer surface of the catheter;

a second telescoping sleeve attached to the sheath, the first telescoping sleeve at least partially extending into the second telescoping sleeve so that the sheath and the catheter are aligned and provide a passageway for a guide wire to move through the guide wire lumen and out through the first and second telescoping sleeves.

22. The apparatus of claim 21, wherein the catheter has a manipulator handle associated with the catheter proximal end, the manipulator handle adapted to move the sheath proximally in relation to the catheter thereby causing the second telescoping sleeve to axially move relative to the first telescoping sleeve.

23. The apparatus of claim 22, wherein the first telescoping sleeve extends into the second telescoping sleeve even after the sheath is moved axially relative to the catheter so that there remains a passageway for the guide wire through the guide wire lumen in the catheter and extending through the first and second sleeves.

* * * * *

UNITED STATES PATENT AND TRADEMARK OFFICE
CERTIFICATE OF CORRECTION

PATENT NO. : 5,993,460
DATED : Nov. 30, 1999
INVENTOR(S) : Rainier Beitelia, Kurt R. Klemm It is certified that error appears in the above-identified patent and that said Letters Patent is hereby corrected as shown below:

Column 1, line 32, change "ofthe", to read --of the--.

Column 3, line 21, change "flirter", to read --further--.

Column 7, line 24, claim 1, change "where in", to read --wherein--.

Signed and Sealed this

Twelfth Day of December, 2000

*Attest:*

Q. TODD DICKINSON

*Attesting Officer*  *Director of Patents and Trademarks*